US00PP28433P2

(12) United States Plant Patent
Miller

(10) Patent No.: US PP28,433 P2
(45) Date of Patent: Sep. 19, 2017

(54) ***SALVIA* PLANT NAMED 'LITTLE KISS'**

(50) Latin Name: *Salvia microphylla*
Varietal Denomination: Little Kiss

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 14/999,678

(22) Filed: Jun. 10, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Cassandra Bright

(57) ABSTRACT

A new and distinct *Salvia* cultivar named 'Little Kiss' is disclosed, characterized by a compact plant form, early flowering and abundant red and white colored flowers. The new variety is a *Salvia microphylla*, normally produced as an outdoor garden or container plant.

2 Drawing Sheets

Latin name of the genus and species: *Salvia microphylla*.
Variety denomination: 'Little Kiss'.

BACKGROUND OF THE INVENTION

The new *Salvia* cultivar is a product of a planned breeding program conducted by the inventor, Luen Miller, in Royal Oaks, Calif. The objective of the breeding program was to produce new *Salvia* varieties with dense plant habits, branch flexibility, strong garden performance, in a range of flower colors. The open pollination resulting in this new variety was made during April of 2009.

The seed parent is the unpatented, *Salvia microphylla* 'Hot Lips'. The pollen parent is unknown as it was an open pollination breeding program. The new variety was identified as a potentially interesting selection in June 2010, at a commercial nursery in Royal Oaks, Calif.

Asexual reproduction of the new cultivar 'Little Kiss' by terminal vegetative cuttings was first performed during Summer of 2010, at a commercial nursery in Royal Oaks, Calif. Subsequent propagation has shown that the unique features of this cultivar are stable and reproduced true to type on successive generations.

SUMMARY OF THE INVENTION

The cultivar 'Little Kiss' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Little Kiss' These characteristics in combination distinguish 'Little Kiss' as a new and distinct *Salvia* cultivar:

1. White flower color with red-blotched lip. Red coloration increasing with flower age.
2. Compact plant form.
3. Abundant flowering.
4. Early flowering.

PARENT COMPARISON

Plants of the new cultivar 'Little Kiss' are similar to plants of the seed parent in most horticultural characteristics, however, plants of the new cultivar 'Little Kiss' differ in the following:

1. Denser and more evenly growing plant than 'Hot Lips'.
2. More compact plant form, shorter mature height than 'Hot Lips'.
3. Earlier flowering than the seed parent.
4. More uniform and abundant flowering than the seed parent.

COMMERCIAL COMPARISON

Plants of the new cultivar 'Little Kiss' can also be compared to the commercial variety *Salvia* 'Bright Eyes', U.S. Plant Pat. No. 22,491. These varieties are similar in most horticultural characteristics; however 'Little Kiss' differs in the following:

1. Plant habit of the new variety is rounder, less upright.
2. More inflorescences per plant.
3. Significantly more white coloration to the flower.
4. Earlier flowering time. The new variety begins flowering in early April compared to first flowering of the comparator in May.

BRIEF DESCRIPTION OF THE PHOTOGRAPHS

Figure 1:
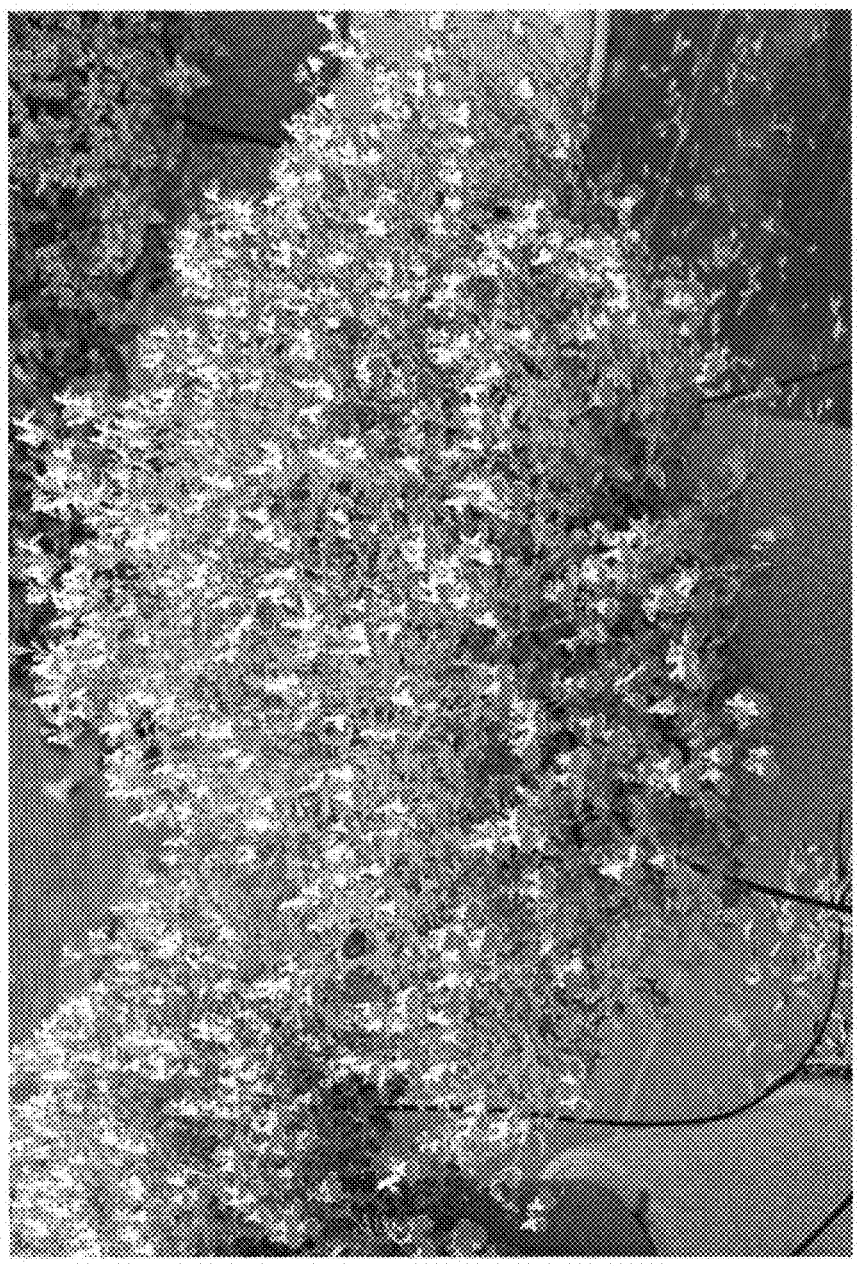

The accompanying photograph in FIG. 1 illustrates in full color a typical mature plant of 'Little Kiss' grown outdoors, in Royal Oaks, Calif., in a commercial 5 gallon container. This plant is shown flowering during May and carries flowers of various stages of maturity.

Figure 2:
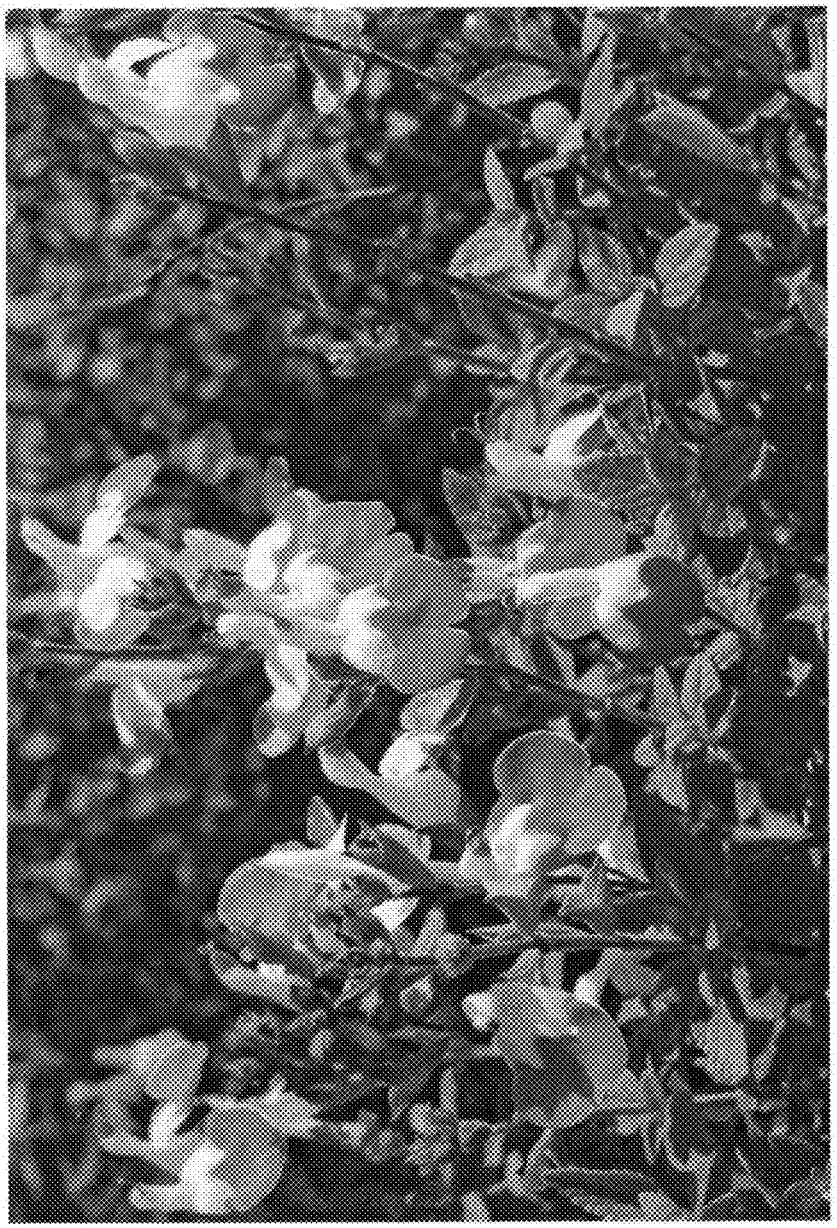

FIG. 2 illustrates in full color typical flowers of 'Little Kiss'.

Age of the plant photographed is approximately 3 years from an unrooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Little Kiss' plants grown outdoors in Royal Oaks, Calif. The growing temperature' ranged from approximately 2° C. to 35° C. Measurements and numerical values represent averages of typical plant types.

Botanical classification: *Salvia microphylla* 'Little Kiss'.

PROPAGATION

Root description: Fine, densely fibrous. Colors include Green-White 157D on new growth and Orange-White 159C, Grey-Brown 199B and 199C for older roots.

PLANT

Growth habit: Semi-upright, round.

Pot size of plant described: 5 gallon pot.

Height: Approximately 40 cm to top of foliage. Approximately 43 cm to top of flowering plane. Measured from soil level of pot.

Plant spread: Approximately 70 cm.

Growth rate: Rapid.

Branching characteristics: Very well branched. Approximately 4 to 6 branches emerging from a pinch, which branch into another 4 to 6 primary lateral branches.

Length of primary lateral branches: Approximately 18 to 30 cm.

Diameter of lateral branches: Approximately 0.4 cm.

Quantity of lateral branches: About 16 to 32.

Stem:

*Color*.—Young growth near RHS Yellow-Green 144C. Mature growth near Greyed-Purple 187A with streaks near Grey-Brown 199B. Grey-Brown color more prominent with age.

*Texture*.—Very slightly hirsute and typically 4 deep ribs. Older growth scaly.

Internode length: Average range 1.5 to 3.0 cm.

Age of plant described: Approximately 1.5 years.

FOLIAGE

Leaf:

*Arrangement*.—Opposite.

*Quantity*.—Average range 12 to 24 fully expanded and immature leaves per main branch with side branches.

*Average length*.—Approximately 2.4 cm. including petiole.

*Average width*.—Approximately 1.3 cm.

*Shape of blade*.—Deltate.

*Apex*.—Acute.

*Base*.—Truncate.

*Attachment*.—Stalked.

*Margin*.—Crenate.

*Texture of top surface*.—Matte, glabrous. Finely reticulated.

*Texture of bottom surface*.—Matte, glabrous. Prominent reticulated veins.

*Color*.—Young foliage upper side: Near RHS Green 137A. Young foliage under side: Near RHS Green 138A. Mature foliage upper side: Near RHS Green 137A. Mature foliage under side: Near RHS Green 138B.

*Venation*.—Type: Reticulate. Venation color upper side: Near RHS Green 137B. Venation color under side: Near RHS Yellow-Green 144B

*Petiole*.—Average Length: Approximately 0.3 cm. Diameter: Approximately 0.1 cm. Color: Near Yellow-Green 144A Other: Foliage moderately aromatic.

FLOWER

Natural flowering season: Flowering from early Spring through late Summer.

Inflorescence type and habit: Flowers arranged in verticillasters.

Flower longevity on plant: Individual flowers last approximately 7 to 10 days on the plant. Each raceme lasts approximately 6 to 8 weeks with flowers. Corolla self-cleaning, calyx persistent.

Quantity of flowers: About 10 to 16 buds and 12 to 20 fully opened flowers per raceme, at one time. Mature plants have approximately 40 to 60 racemes.

Raceme size:

*Diameter*.—Approximately 3.5 cm.

*Height*.—Approximately 5.0 to 9.0 cm.

Individual flowers:

Size:

*Diameter*.—Approximately 1.4 cm.

*Length*.—Approximately 2.5 cm.

Fragrance: Faint aromatic scent.

Corolla:

*Petal arrangement*.—The corolla is sympetalous and typically bilabiate with 2 small, fully fused lobes forming a single upper lip and 3 larger fused lobes forming a lower lip.

*Margin*.—Entire.

*Tip shape*.—Upper lip tip obtuse, lower lip tip retuse.

*Length*.—Upper lip Approximately 0.7 cm. Lower lip Approximately 0.9 cm. Tube length Approximately 1.5 cm.

*Width*.—Upper lip: Approximately 0.4 cm, lower lip Approximately 1.3 cm. Tube width: Approximately 0.5 cm.

*Texture*.—Upper lip: Glabrous all surfaces. Lower lip: Glabrous all surfaces.

Color:

*Upper lip*.—When opening: Inner surface: Near RHS White N155D. Outer surface: Near RHS White N155D. Fully opened: Inner surface: Near RHS White N155D. Outer surface: Near RHS White N155D. Fading: Inner surface: Near RHS White N155D. Outer surface: Near RHS White N155D.

Color:

*Lower lip*.—When opening: Inner surface: Near RHS White N155D, apex blotched Red 45A. Outer surface: Near RHS White N155D, apex blotched Red 45A. Fully opened: Inner surface: Near RHS White N155D, apex blotched Red 46A. Outer surface: Near RHS White N155D, apex blotched Red 46A. Fading: Inner surface: Near RES White N155D, apex blotched Red 53A. Outer surface: Near RHS White N155D, apex blotched Red 53A.

Color:

*Tube*.—When opening: Inner surface: Near RHS White N155D. Outer surface: Near RHS White N155D. Fully opened: Inner surface: Near RHS White N155D. Outer surface: Near RHS White N155D. Fading: Inner surface: Near RHS White N155D. Outer surface: Near RHS White N155D.

Bud: Flower bud includes immature calyx which completely surrounds immature corolla.

*Shape*.—Ovoid.

*Length*.—Approximately 1.4 cm.

*Diameter*.—Approximately 0.5 cm.

*Color*.—Near RHS White N155A, lightly blotched Red 45A.

Calyx:

*Length*.—Approximately 1.0 cm.

*Diameter*.—Approximately 0.5 cm.

*Shape*.—Tubular.

Sepals:

*Shape*.—Quantity per flower: 3, fused to form a tube. Unfused apex.

*Length*.—Approximately 0.3 cm unfused portion.

*Width*.—Approximately 0.2 cm.

*Margin*.—Entire.

*Apex*.—Short apiculate.

*Texture*.—Slightly hirsute and ridged.

*Color*.—Immature: Near Green 143C, apiculate point near Greyed-Purple N187A. Mature: Near Green 143C, apiculate point near Greyed-Purple N187A.

Peduncle:

*Length*.—Average 2.0 cm.

*Diameter*.—0.3 cm.

*Color*.—One side typically near RHS Yellow-Green 144B.

*Orientation*.—Straight or very slightly curved. Occurring at approximately 15 degree angle from center of plant.

*Strength*.—Moderately strong.

*Texture*.—Very slightly hirsute, ridged.

Pedicels:

*Length*.—Average range 0.2 to 0.3 cm.

*Diameter*.—0.1 cm.

*Color*.—Near RHS Green 143C.

*Orientation*.—Straight, approximately 15 degree angle from attachment.

*Strength*.—Strong.

*Texture*.—Glabrous.

REPRODUCTIVE ORGANS

Stamens:

*Number*.—2.

*Filament length*.—Approximately 0.3 cm.

*Filament color*.—Near RHS White N155B.

Anthers:

*Shape*.—Linear.

*Length*.—0.1 cm.

*Color*.—Near RHS Orange-Red 34B.

*Pollen*.—Moderate pollen observed, colored near RHS Orange-Red 34B.

Pistil:

*Number*.—1.

*Length*.—Approximately 2.0 cm.

*Style*.—Length: Approximately 1.8 cm. Color: Near RHS White N155D.

*Stigma*.—Shape: Forked. Color: Near RHS Red 53B. Ovary: Colored near RHS Yellow-Green 145D, oblong, approximately 0.2 cm long and 0.1 in diameter.

OTHER CHARACTERISTICS

Seeds and fruits: Very little seed production. Occasionally a single seed is produced. Oblong, approximately 4 mm long, 2 mm wide. Colored near Brown 200A.

Disease/pest resistance: Neither resistance nor susceptibility to pathogens and pests common to *Salvia microphylla* have been observed.

Temperature tolerance: The new variety tolerates temperatures within USDA zones 3 to 8.

What is claimed is:

1. A new and distinct cultivar of *Salvia* plant named 'LITTLE KISS' as herein illustrated and described.

* * * * *